United States Patent
Shabanov et al.

(10) Patent No.: US 9,382,494 B2
(45) Date of Patent: *Jul. 5, 2016

(54) METHODS FOR REDUCING HEAVY OIL VISCOSITY

(71) Applicant: Asiacom Group Investments, Inc., Oklahoma City, OK (US)

(72) Inventors: Alimamed L. Shabanov, Baku (AZ); Elmira M. Ramazanova, Baku (AZ); Ulviyya A. Gasanova, Baku (AZ)

(73) Assignee: ASIACOM GROUP INVESTMENTS, INC., Oklahoma City, OK (US)

( * ) Notice: Subject to any disclaimer, the term of this patent is extended or adjusted under 35 U.S.C. 154(b) by 57 days.

This patent is subject to a terminal disclaimer.

(21) Appl. No.: 14/451,567

(22) Filed: Aug. 5, 2014

(65) Prior Publication Data

US 2014/0345192 A1 Nov. 27, 2014

Related U.S. Application Data

(60) Continuation-in-part of application No. 13/799,096, filed on Mar. 13, 2013, now Pat. No. 8,801,811, which is a division of application No. 12/536,076, filed on Aug. 5, 2009, now Pat. No. 8,420,837.

(51) Int. Cl.

| | | |
|---|---|---|
| *C10L 10/02* | (2006.01) | |
| *C07F 15/02* | (2006.01) | |
| *C07D 413/12* | (2006.01) | |
| *C07D 273/02* | (2006.01) | |
| *C07D 498/08* | (2006.01) | |
| *C09K 8/58* | (2006.01) | |
| *C10M 159/18* | (2006.01) | |
| *C09K 8/00* | (2006.01) | |
| *C10M 139/06* | (2006.01) | |
| *C10L 1/30* | (2006.01) | |

(52) U.S. Cl.
CPC ............. *C10L 10/02* (2013.01); *C07D 273/02* (2013.01); *C07D 413/12* (2013.01); *C07D 498/08* (2013.01); *C07F 15/025* (2013.01); *C09K 8/00* (2013.01); *C09K 8/58* (2013.01); *C10L 1/301* (2013.01); *C10M 139/06* (2013.01); *C10M 159/18* (2013.01); *C09K 2208/10* (2013.01); *C10L 2200/024* (2013.01); *C10L 2230/14* (2013.01); *C10M 2227/09* (2013.01); *C10N 2220/082* (2013.01); *C10N 2230/02* (2013.01); *C10N 2230/12* (2013.01)

(58) Field of Classification Search
CPC ..................... C10M 2227/09; C10L 2200/024
USPC ........................................................... 44/363
See application file for complete search history.

(56) References Cited

U.S. PATENT DOCUMENTS

| | | | | |
|---|---|---|---|---|
| 7,712,528 | B2 * | 5/2010 | Langdon ................. | E21B 36/02 166/263 |
| 8,333,945 | B2 * | 12/2012 | McLaughlin .......... | B82Y 30/00 423/263 |
| 8,420,837 | B2 * | 4/2013 | Shabanov ............. | C07D 273/02 549/200 |
| 8,801,811 | B2 * | 8/2014 | Shabanov ............. | C07D 273/02 44/329 |
| 2010/0212221 | A1 * | 8/2010 | Aradi ..................... | B82Y 30/00 44/500 |
| 2011/0155643 | A1 * | 6/2011 | Tov ........................ | B01D 3/009 208/119 |
| 2013/0337998 | A1 * | 12/2013 | Irving .................... | B01J 13/003 502/167 |
| 2014/0027116 | A1 * | 1/2014 | Suresh ..................... | C09K 8/56 166/292 |

OTHER PUBLICATIONS

Mirzadjanzade, Studying of influence of iron nanoparticles and aluminum, [date unknown].
Ramazanova, The application of iron nanocomposite in oil industry and petroleum chemistry, "Khazarneftyatag-2008" Nov. 4, 2008.
Shabanov, Progress in crown compounds chemistry, 10th annual Florida Heterocyclic Conference, Mar. 2009.
Shabanov, Metalation of Toluene and Cumene with Alkali Metal-Crown Ether Compounds, Russian Journal of Organic Chemistry, 2009, vol. 45, No. 1, pp. 26-29.

* cited by examiner

*Primary Examiner* — Ellen McAvoy
(74) *Attorney, Agent, or Firm* — ColterJennings

(57) ABSTRACT

A stabilized nano-$Fe_6$-iron-crown ether complex is added to a heavy oil to reduce the viscosity of the heavy oil. The complex may be formed by preparing a solution of an iron salt and an oligomer crown compound in dialkylamine or diethylamine. Sodium tetrahydroboron ($NaBH_4$) and dialkylamine or ethylendiamine are added at a temperature of 0-10° C. The mixture is heated to room temperature and boiled, thereby converting the formed iron (II)-borhydride complex (Fe$(BH_4)_2$) to a crown ether—iron-hydride complex $[CWFe^0_6]$. $(2H)_6$. At higher temperature this last complex is converted to the $Fe^0_6$-crown nanocomposite complex. The prepared nanoparticle $Fe_6^0$ complex may be stabilized by inclusion into a cavity of a macrocyclic compound, and may be (1) added to diesel fuel to reduce NOx emissions upon combustion of that fuel; (2) added to lubricating oils as an anticorrosion additive; and (3) used as an additive to secondary recovery processes within liquid hydrocarbon formations to increase the sweep efficiency and recovery factor of water-flooding operations.

3 Claims, No Drawings

METHODS FOR REDUCING HEAVY OIL VISCOSITY

CROSS-REFERENCE TO RELATED APPLICATION

This application is a continuation-in-part of application Ser. No. 13/799,096 filed Mar. 13, 2013, which was a division of application Ser. No. 12/536,076, filed Aug. 5, 2009, now U.S. Pat. No. 8,420,837, the disclosures of both of which are incorporated herein by this reference.

BACKGROUND

This invention relates to a phase-transfer catalytic method for preparing a nanoparticle iron—crown ether complex, and in particular to use of the resulting complex in reducing viscosity in an oil field environment.

Previously, nanoparticle iron ($Fe_6^0$) has been synthesized from salts based on reduction of iron with $NaBH_4$. This preparation method is typically slow, and generally provides relatively low yields of the iron nanoparticle. This preparation method often does not allow for stabilization of the prepared nanoparticle. Lack of stabilized materials may quickly reduce the activity of the prepared nanoparticle.

Typically, the process is carried out in aqueous solutions. This reduces the yield and activity of the nanoparticle iron. These disadvantages of prior processes reduce the commercially viability of a continuous process $Fe_6$ nanoparticle production system. A need exists, therefore, for a high-yield catalytic process for producing stabilized nanoparticles, particularly $Fe_6$ from iron salts.

SUMMARY

A method of preparing a nanoparticle iron—crown ether complex uses an organic solvent and oligomer crown compounds as a stabilizer. A solution of an iron salt, such as Mor salt, and an oligomer crown compound are mixed in an organic solvent, such as dialkylamine or diethylamine, at room temperature. Sodium tetrahydroboron in diethylamine is added and mixed.

The mixture is then boiled to remove diethylamine and the mixture is filtered under a nitrogen atmosphere. Ethanol is added, and the excess sodium tetrahydroboron removed. This causes the formation of an iron-nanoparticle-crown ether complex that retains activity of the nanoparticle iron. The crown ether oligomer also assists in regulating the selectivity of iron nanoparticle formation during the process.

DETAILED DESCRIPTION

The present method involves preparation of nanoparticles, and in particular nanoparticles of $Fe_6$ using oligomer crown ethers as a stabilizer. The method results in relatively high yields, often greater than 70%, and also provides a stabilizer for retaining the activity of the nanoparticle iron. The method produces nanoparticle $Fe_6$ from iron salts by reduction with sodium tetrahydroboron ($NaBH_4$) in dialkylamine in the presence of crown ethers.

The present method incorporates a two-phase process for $Fe_6$, a hard phase and an organic phase. The hard phase is that of an iron salt. The organic phase involves dry dialkylamine, or ethylene diamine, containing an oligomer crown ether [I]. The crown-compound I complexes with the iron salt to transfer the iron salt from the hard phase to a dialkylamine organic phase as complex II. Adding sodium tetrahydroboron to the organic phase at low temperatures (0-10° C.) causes the formation of an iron—crown ether complex III. The iron salt may be the Mor salt, $FeSO_4 x(NH_4)_2SO_4 x6H_2O$, $FeBr_2$, or other iron-organic compounds. The crown compound may be those that form stable complexes with iron salts can be used as stabilizer of iron nanoparticles, such as [2,2,2]-cryptand, [2,2,1]-cryptand, oligomer crown compounds, containing two nitrogen atoms in macrocyclic ring.

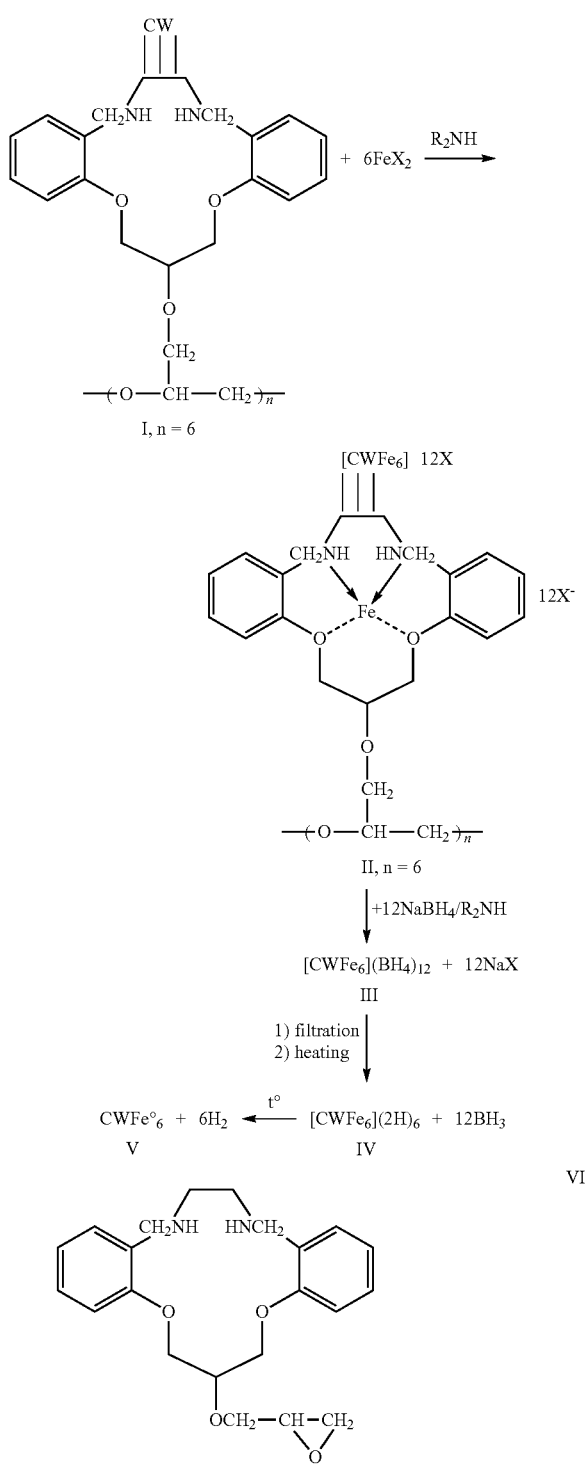

After separation of the resulting NaX by filtration of the organic phase and heating of the reaction mixture to a boiling temperature, the complex III is converted to a crown ether-iron-hydride complex IV. The hydride complex IV is then heated to approximately 115-120° C., decomposing the hydride complex IV and resulting in the oligomer crown ether I and the $Fe_6$ nanocomposite V.

In a metal, the individual metal atoms are typically closely packed together, that is, each individual metal atom is typically surrounded by a large number of similar atoms (often 6 or 8 or 12 atoms surround each individual metal atom). The bulk metal may be pictured as consisting of positively charged atoms embedded in a "sea" of free valence electrons. There are, therefore, no localized bonds, as there are in a large covalent crystal like diamond. The freedom of the electrons is demonstrated by their ability to move in an electrical field, so bestowing electrical conductance on the metal. That appears to be the reason positively charged metal atoms can be captured by a cryptand or crown ether cavity. Additionally, a metal can be viewed as a massive body, similar to a polymer. In the process of destruction of a metal's "massive body" during interactions, corresponding cells are formed. As result of such interaction CW with iron nanoparticles, homopolyatomic iron anions are formed.

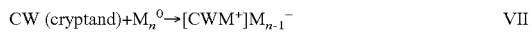

CW (cryptand)+$M_n^0$→[$CWM^+$]$M_{n-1}^-$     VII

As a result of conversion of formed $CWFe^0{}_n$ (n=6 and more) to ion pair complex VII, positive metal atoms move or are included into the crown ether cavity, and the remaining metal atoms have a negative charge and remain on the outer periphery of complex. The essential nature of the process perhaps may be creation of a metal-cryptand complex along the lines of:

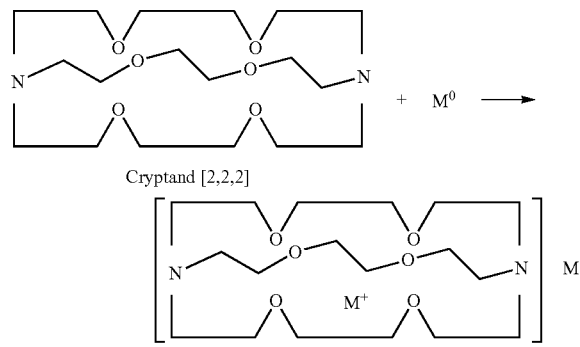

Cryptand [2,2,2]

The resulting oligomer crown ether-nano-iron composition is useful in an oil field environment. In particular, the complex may be used as a reagent to reduce the viscosity of heavy oils. The composition thus increases oil recovery and transportation of heavy oils in general, and in particular at low temperatures, such as during cold weather.

EXAMPLES

Example 1

Each experiment was conducted in a glass reactor under a nitrogen atmosphere. To a mixture of 1.80 g (0.003 mol) of the Mor salt ($FeSO_4$ ($NH_4$)2 $SO_4$.$6H_2O$) and 4.6 g (0.0012 mol) oligomer crown compound I in 60 ml of dialkylamine or diethylamine at −10° C. was added 0.25 grams (0.007 mol) sodium tetrahydroboron in 15 ml of amine. The mixture was stirred for 40 min. Typically, ethylene diamine is used, but dialkylamines may also be used, though thus far they have produced lower yields. After adding sodium tetrahydroboron dialkylamine or ethylene diamine, over a period of forty minutes, the reaction mixture was mixed for an additional 2 hours. The mixture was heated to room temperature and boiled for 1.5 hours.

The reaction mixture was then filtered under a nitrogen atmosphere, after which 5 ml of ethanol was added for destruction of excess $NaBH_4$. In addition, approximately one-half of the solvent was also removed to precipitate the iron nanocomposite (that is, the nanoparticle iron—crown compound complex). The solution was cooled to 5° C. to precipitate 3.48 g (73%) of the particulate iron-crown composite V having a black color.

The composition of this compound V was confirmed with element analysis:

Found, % C=59.72, H=6.52, N=6.05, Fe=12.56, $C_{132}H_{168}O_{24}N_{12}Fe_6$.

Calculated, % C=60, H=6.36, N=6.36, Fe=12.7.

The mass-spectrum of the resulting product showed no lines of ordinary iron monomer but did show line 335.04, confirming the presence of $Fe_6$ in the composition of CW $Fe_6^0$ (V). The prepared composition is pyrophorous and has high chemical activity. It has been shown that $Fe_6$-nanoparticle complexed with CW is amorphous and there is no usual iron line in its x-ray spectrum.

The presence of electroneutral nano-iron particles $Fe^0{}_6$ in the nanocomposite $CWFe^0{}_6$ has been determined by a known method (see A. Ch. Mirzadjanzade, A. L. Shabanov and et. al "Studying the influence of nanoparticles of iron to the process of increasing of intensity of gas elimination and layer pressure with the purpose application in oil recovery, News of Baku University. 2005. #1. p. 5-13). According to this method, electroneutral $Fe^0{}_6$ in composite is converted to a stable nano-homopolyatomic anion of $Fe^-{}_6$ by interaction between $CWFe^0{}_6$ and [$CWK^+$]$K^-{}_7$ nanocomplex according to the equation:

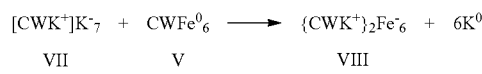

[$CWK^+$]$K^-{}_7$ + $CWFe^0{}_6$ ⟶ {$CWK^+$}$_2Fe^-{}_6$ + $6K^0$
   VII              V                    VIII (See, A. L. Shabanov and et al., J. Org. Chemistry. (Saint Petersburg, Russia). 2009. #1; and A. L. Shabanov, Invited lectures in the 10$^{th}$ Annual Florida Heterocyclic and Synthetic Conference. Mar. 8-11, 2009, p. 48.)

The presence of the complex VIII having a mol relation between $K^+$ and $Fe^-{}_6$ has been found by atom-absorption analysis, showing a ratio of 2:6. Thus, the initial nanocomposite, from which the last complex VIII was prepared, has the composition and structure shown in V. The size of the iron-nanoparticles were determined by AFM spectroscopy to be approximately ≈35-75 nm.

As a comparative example, the nanocomplex [$CWK^+$]$K^-{}_7$ was prepared as described in A. L. Shabanov and et al., J. Org. Chemistry. (Saint Petersburg, Russia). 2009. #1. The method described was also used, except that the oligomer diazacrown ether I was replaced with the monomer diazacrown ether VI. The yield decreased by 21%. By way of explanation, possibly the "cavity" of the monomer diazacrown ether VI is too small for sufficient binding with the $Fe_6$ nanoparticle, whereas the comparatively large cavity of the oligomer crown compound I comfortably ties together with the $Fe_6$ nanoparticle. Thus, it appears that the oligomer crown compound I may be an effective stabilizer for the nanoparticle $Fe_6$.

Example 2

A mixture of 2.3 g (0.001 mol) crown compound (I) and 10.9 g (0.0015) Mor salt in 30 ml of ethylene diamine was mixed with 8 ml of amine containing 1.25 g (0.0035 mol) of $NaBH_4$ at $-10°$ C. The mixture was stirred for an additional two hours, heated to room temperature, and then boiled for 1.5 hours. The product was filtered under a nitrogen atmosphere. Approximately half the solvent was removed and the solution cooled to precipitate out 1.75 g (72%) of the particulate iron-crown composite V having a black color.

Example 3

Using the same methodology, 4.0 g of nanocomposite V was prepared from the initial compound I in 50 ml of diethylamine, 142 g Mor salt and 0.3 g sodium tetrahydroboron ($NaBH_4$). Example 4. Using the same method, 4.67 g of nanocomposite was prepared from 3.5 g of oligomer crown compound I in 60 ml of ethylenediamine, with 1.35 g Mor salt and 0.3 g NaBH4.

Because of the basity and the small size of the negatively charged Fe ions, the Fe ions are able to penetrate into the pores of oil bearing strata, and react with water according to the reaction:

$$Fe^0{}_6 + 12HOH \rightarrow 6H_2 + 6Fe(OH)_2.$$

Thus, the nano Fe causes hydrogen liberation. This hydrogen gas increases the pressure in the strata, resulting in better oil recovery.

As a result, when used in water injection secondary recovery techniques, the nanocomposite CWFe6 increases the sweep efficiency of the "fluid front" as it moves through the oil zone from the injection wells towards the producing wells. Sweep efficiency relates to the mobility ratio of the oil to the water. Water typically has a higher mobility and therefore tends to bypass some of the oil leaving a "high residual oil saturation" in the strata. There are ways to improve this, such as miscible flooding by adding carbon dioxide or surfactants to the injected water. This is effective but very expensive.

However, by adding small amounts (such as 0.05-0.1%) of the Fe nanoparticle composite to the water, when the water enters the pore spaces of the reservoir rock, the Fe nanoparticles leave the complex in an active and reactive state. The nanoparticles improve the mobility of the oil pore volume saturation and also cause a local increase in pore pressure. Both these effects improve the mobility of the oil saturation in relation to the water mobility and result in improved sweep efficiency, more effective oil bank formation, and lower residual oil saturation. The result is higher produced oil rates and higher cumulative oil production from the oil zone.

The highly reactive nature of the negatively charged Fe ions may also be useful for other processes. For instance, the complex may be used in the reduction of $NO_x$ molecules, according to the formula:

As electrons fill orbitals, the $[CWFe_6{}^{2+}][N{=}O]_6{}^{2-}$ complex (IX) disintegrates, restoring the catalyst $CWFe_6$ using electrons from the nano-iron according to the formula:

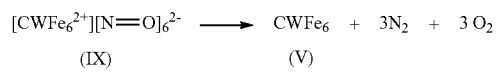

As a result, the nanoiron-crown ether complex V is an effective additive for diesel fuel to reduce $NO_x$ emissions. Adding a small amount (such as a concentration of 0.005-0.01%) of the Fe nanoparticle complex to diesel fuel may reduce 75-90% of $NO_x$ emissions.

Example 4

Tests were conducted in the Siazan oil field (SOCAR, Azerbaijan). 0.05% of the reagent Fe nanoparticle composite were injected into the oil. As result of such injection, the viscosity of the oil decreased 40-80% (independent of oil composition). In another case, 0.5 g of the nanoiron Fe6 particle dispersion was added to 10 ml of an alkali solution of petrochemical industry waste products. The prepared solution was mixed with 200 ml of heavy oils. The initial viscosity of the heavy oil was 14.5 sst (at 20°). After addition of the 10 ml of prepared solution, the oil viscosity dropped to 3.5 sst. Similar viscosity decreases will occur in a storage tank environment, that is, as the oil is poured into a storage tank, or is being held in a storage tank. In another example, injection of a 4.5% nanoiron dispersion in an alkali solution of petrochemical industry waste into an old oil well increased oil recovery by 240%.

Addition of nanoiron-crown complex (V) also improves anticorrosion properties of lubricating oils. Thus, the present method has several advantages over the prior art and over reactions that do not involve the catalyst. Although embodiments of the present method have been described, various modifications and changes may be made by those skilled in the art without departing from the spirit and scope of the invention.

The invention claimed is:

1. A method of reducing the viscosity of a heavy oil comprising the step of injecting a nanoparticle $Fe^0{}_6$-crown ether complex into the heavy oil.

2. The method of claim 1 in which the $Fe^0{}_6$-crown ether complex is prepared by a method comprising the steps of:
   preparing dialkylamine or ethylenediamine solutions of iron (II) complexes with olygomer crown ethers, containing two nitrogen atoms in macrocyclic ring at a first predetermined temperature;
   adding a predetermined amount of a solution of sodium tetrahydroboron in ethylene diamine and mixing the result for a first predetermined period of time;
   heating the resulting mixture to a second predetermined temperature and then boiling the mixture for a second predetermined period of time;
   filtering the resulting mixture under a nitrogen atmosphere;
   adding ethanol to the resulting mixture to reduce excess $NaBH_4$, and continuing to boil the mixture until at least half of the ethylene diamine has been removed; and
   cooling the mixture to below 5° C. to precipitate a nanoparticle $Fe^0{}_6$-crown ether complex $CWFe_6$.

3. The method of claim 1 in which the complex is added to heavy oil in a storage tank environment.

* * * * *